US009592552B2

(12) United States Patent
Choi

(10) Patent No.: US 9,592,552 B2
(45) Date of Patent: Mar. 14, 2017

(54) METHOD OF NEUTRALIZING AMINE GAS ODOR IN COLD BOX PROCESS, AND AMINE GAS GENERATOR USING THE SAME

(71) Applicant: ABC CO., LTD., Ulsan (KR)

(72) Inventor: Jae-young Choi, Busan (KR)

(73) Assignee: ABC Co., Ltd. (KR)

( * ) Notice: Subject to any disclaimer, the term of this patent is extended or adjusted under 35 U.S.C. 154(b) by 0 days.

(21) Appl. No.: 14/699,118

(22) Filed: Apr. 29, 2015

(65) Prior Publication Data

US 2016/0214168 A1    Jul. 28, 2016

(30) Foreign Application Priority Data

Jan. 23, 2015    (KR) .................. 10-2015-0011241

(51) Int. Cl.
*A61L 2/00*    (2006.01)
*A61L 9/00*    (2006.01)
*B22D 45/00*    (2006.01)
*B22C 9/12*    (2006.01)

(52) U.S. Cl.
CPC .............. *B22D 45/005* (2013.01); *A61L 9/00* (2013.01); *B22C 9/123* (2013.01)

(58) Field of Classification Search
CPC ........................................................ A61L 2/00
USPC .................. 422/1, 5, 292, 300, 305; 53/510
See application file for complete search history.

(56) References Cited

U.S. PATENT DOCUMENTS

2004/0237478 A1\*    12/2004    Rossi .................... B65B 31/028
                                                                   53/510

\* cited by examiner

*Primary Examiner* — Monzer R Chorbaji
(74) *Attorney, Agent, or Firm* — Park & Associates IP Law, P.C.

(57) ABSTRACT

A method of neutralizing an amine gas odor in a cold box process, and an amine gas generator using the method are disclosed. The method includes: making molding sand by mixing sand and forming resin; putting the molding sand into a mold; hardening the molding sand by injecting an amine gas into the molding sand in the mold; and removing an amine gas odor remaining in the mold by injecting an amine gas odor neutralizer into the mold. Accordingly, it is possible to inject an amine gas odor neutralizer in casting of a core or a mold in order to reduce the amine gas odor that remains and leaks through a gap of a mold in the casting. Further, an odor neutralizer is immediately injected simultaneously with discharging of an amine gas, so it is possible to simply remove an odor.

6 Claims, 3 Drawing Sheets

METHOD OF NEUTRALIZING AMINE GAS ODOR IN COLD BOX PROCESS, AND AMINE GAS GENERATOR USING THE SAME

REFERENCE TO RELATED APPLICATIONS

This application claims the priority benefit of Korean Patent Application No. 10-2015-0011241 filed on Jan. 23, 2015, the entire contents of which are incorporated herein by reference.

FIELD OF THE INVENTION

The present invention relates to a method of neutralizing an amine gas odor in a cold box process and a gas generator using the method. More particularly, the present invention relates to a method of neutralizing an amine gas odor in a cold box process that injects an odor neutralizer for an amine gas after hardening in order to reduce the amine gas odor that remains or leaks through a gap of a mold in the processing of manufacturing a core or a mold, and an amine gas generator using the method.

BACKGROUND OF THE INVENTION

A mold used for making the shape of a hole for manufacturing a hollow part such as a column in general casting is called a core. Casting for manufacturing a hollow cast is made by putting a core into a mold, injecting molten metal into the mold, taking out the cast and the core from the mold after the molten metal hardens, and then separating the core from the cast.

A core or a mold for casting is manufactured, for example, by making molding sand, in which dry sand and a plurality of forming resins are uniformly mulled by a mixer, putting the molding sand into a mold, hardening the molding sand by injecting an amine gas into the molding sand in the mold, and taking out the hardened object.

Such a technique has been disclosed in Korean Patent No. 10-1131033, titled "Use of amine blends for foundry shaped cores and casting metals". In this related art, phenolic resin and polyisocyanate are used as a forming resin, and molding sand is obtained by mixing the forming resin with sand. The molding sand is hardened at room temperature, using an amine blend as a hardener and a core or a mold made of polyurethane can be obtained through the hardening. This process is called a PUCB (Polyurethane Cold Box) process.

Hardening a core or a mold using an amine gas has various advantages, for example: it can be hardened at room temperature without heating at a high temperature, the hardening speed is higher than high-temperature hardening, and not only the surface of molding sand, but the entirety of the molding sand can be hardened. However, when an amine gas is used as a hardener, a worker may have difficulty in working due to the amine gas odor remaining after hardening or due to an amine gas leak through a gap of a mold.

Documents of Related Art (Patent Document 1) Korean Patent No. 10-1131033
(Patent Document 2) Korean Patent Application Publication No. 10-2009-0011520

SUMMARY OF THE INVENTION

Accordingly, the present invention has been made keeping in mind the above problems occurring in the related art, and the present invention is intended to propose a method of neutralizing the odor of an amine gas for a cold box process that injects an odor neutralizer for an amine gas after hardening in order to reduce the odor of an amine gas that remains or leaks through a gap of a molding in a processing of manufacturing a core or a mold, and an amine gas generator using the method.

Further, the present invention provides a method of neutralizing an odor of an amine gas for a cold box process that can simply remove an odor by injecting an odor neutralizer directly into a mold simultaneously with discharge of an amine gas, and an amine gas generator using the method.

In order to achieve the objects of the present invention, there is provided a method of neutralizing an odor of an amine gas for a cold box process that includes: making molding sand by mixing sand and forming resin; putting the molding sand into a mold; hardening the molding sand by injecting an amine gas into the molding sand in the mold; and removing an amine gas odor remaining in the mold by injecting an amine gas odor neutralizer into the mold.

In the removing the amine gas odor, the odor neutralizer may be injected into the mold simultaneously with discharging of the amine gas to the outside from the mold and an amount of the odor neutralizer injected may be 5 to 15 parts by weight based on 100 parts by weight of the amine gas.

In order to achieve the objects of the present invention, there is provided an amine gas generator that includes: an amine supplier supplying a stored amine gas; an odor neutralizer supplier supplying an odor neutralizer for removing the amine gas odor; an injection line through which the amine gas or the odor neutralizer is injected with compressed air into a mold; a regulator disposed in the injection line and maintaining an injection pressure of the compressed air at a predetermined level; a first valve disposed between the amine supplier and the injection line and stopping or passing the amine gas; and a second valve disposed between the odor neutralizer supplier and the injection line and stopping or passing the odor neutralizer.

The injection line may be divided into a gassing line through which the amine gas is injected with heated-compressed air into the mold and a purging line through which the odor neutralizer is injected with heated-compressed air into the mold, and the regulator may be composed of a first regulator disposed in the gassing line and maintaining injection pressures of the amine gas and the compressed air at predetermined level and a second regulator disposed in the purging line and maintaining injection pressures of the odor neutralizer and the compressed air at predetermined levels.

The amine gas generator may further include a third valve disposed in the gassing line and stopping or passing the compressed air and a fourth valve disposed in the purging line and stopping or passing the compressed air, and may further include a first check cylinder disposed in the gassing line for checking a supply amount of the amine gas and a fourth valve disposed in the purging line for checking a supply amount of the odor neutralizer, and the second valve may open simultaneously with closing of the first valve so that the odor neutralizer is supplied.

The first valve may have a first valve timer for adjusting opening and closing of the first valve at predetermined times and the second valve may have a second valve timer for adjusting opening and closing of the second valve at predetermined times. The amine gas generator may further include an air tank supplying the compressed air and an air heater heating the compressed air discharged from the air tank at 40 to 100° C.

According to the present invention, it is possible to inject an amine gas odor neutralizer after hardening in order to reduce the amine gas odor that remains and leaks through a gap of a mold in a process of manufacturing a core or a mold.

Further, an odor neutralizer is immediately injected simultaneously with discharging of an amine gas, so it is possible to simply remove an amine gas odor.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinafter, a method of neutralizing an amine gas odor for a cold box process according to the present invention and amine gas generators 100 and 200 using the method will be described in detail with reference to the accompanying drawings.

Figure 1:
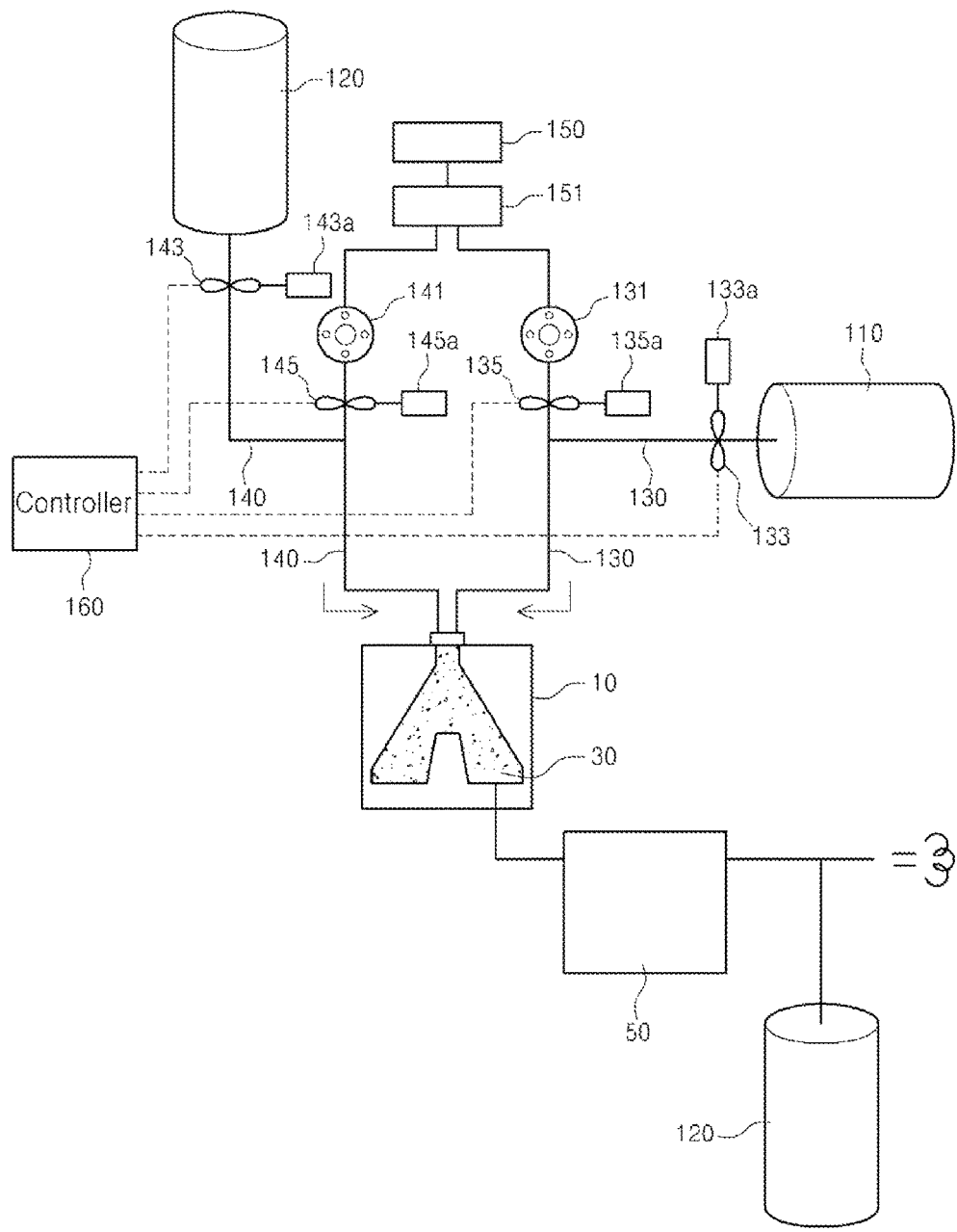
FIG. 1 is a view of an amine gas generator according to a first embodiment of the present invention.

First, as shown in FIG. 1, an amine gas generator 100 according to a first embodiment includes an amine gas supplier 110 storing an amine gas, an odor neutralizer supplier 120 supplying an amine gas odor neutralizer, and a gassing line 130 and a purging line 140 through which an amine gas is injected into a mold 10.

An amine gas in the amine gas supplier 110 is supplied to the mold 10 through the gassing line 130. A first regulator 131 connected to an air tank 150 and receiving compressed air from the air tank 150 to maintain the pressure of injected amine gas at a predetermined level is disposed in the gassing line 130.

As compressed air passes through the first regulator 131 from the air tank 150 for supplying the compressed air, the first regulator 131 adjusts the pressure of the compressed air to a predetermined level, and when the compressed air is sent into the mold 10, an amine gas is supplied into the mold 10 with the compressed air by the pressure of the compressed air.

The generator further includes an air heater 151 that heats the compressed air from the air tank 150 at 40 to 100° C., when it flows into the gassing line 130. When the temperature of the compressed air is lower than 40° C., an odor neutralizer may turn to liquid, and when it is higher than 100° C., the amine generator 100 may be damaged. Accordingly, it is important to maintain and supply compressed air at an appropriate temperature using the air heater 151.

A first valve 133 stopping/passing an amine gas is disposed between the amine supplier 110 and the gassing line 130. When the first valve 133 is open, an amine gas is supplied to the gassing line 130 from the amine generator 110, and when the first valve 133 is closed, an amine gas is not supplied to the gassing line 130 from the amine supplier 110. The first valve 133 has a first valve timer 133a that opens/closes the first valve at predetermined times.

A third valve 135 that opens/closes the gassing line 130 is disposed in the gassing line 130. The third valve 135 opens or closes to adjust the amount of the compressed air that has passed through the first regulator 131, so the compressed air and the amine gas that are supplied into the mold 10 are adjusted. The third valve 135 may have a third valve timer 135a that controls opening/closing of the third valve 135 at predetermined times.

The supply amount of an amine gas adjusted by the first valve 133 can be checked through a first check cylinder, if necessary. The check cylinder comes from the gassing line 130 and it is possible to check the supply amount of an amine gas in real time, using a graduation marked on the first check cylinder.

A second regulator 141 that maintains the compressed air from the air tank 150 at a predetermined pressure is disposed in the purging line 140. Similar to the first regulator 131, as compressed air passes through the second regulator 141 from the air tank 150, the second regulator 131 adjusts the pressure of the compressed air to a predetermined level, and when the compressed air is sent into the mold 10, an odor neutralizer is supplied into the mold 10 with the compressed air by the pressure of the compressed air.

A second valve 143 stopping/passing an odor neutralizer is disposed between the amine neutralizer supplier 120 and the purging line 140. Similar to the first valve 133, when the second valve 143 is open, an odor neutralizer is supplied into the purging line 140, and when the second valve 143 is closed, an odor neutralizer is not supplied. The second valve 143, similar to the first valve 133, has a second valve timer 143a.

A fourth valve 145 that opens/closes the purging line 140 is disposed in the purging line 140. The fourth valve 145 adjusts supply and stoppage of the compressed air that has passed through the second regulator 141. The fourth valve 145 may have a fourth valve timer 145a that controls opening/closing of the fourth valve 145.

The supply amount of the odor neutralizer adjusted by the third valve 143 and the fourth valve 145 can be checked by the second check cylinder, similar to the first check cylinder.

When the amount of an amine gas supplied to the mold 10 and checked through the first check cylinder reaches to a predetermined level, the supply of the amine gas is stopped by the first valve 133 or the third valve 135. Further, when the information about the supply amount of the amine gas is transmitted to a controller 160 or a user inputs it to the controller 160, the controller 160 sends a signal to the second valve 143 or the fourth valve 145 so operate them. When the supply of the amine gas is stopped, the compressed air and the odor neutralizer are injected into the mold 10.

The second valve 143 or the fourth valve 145 may operate such that the odor neutralizer is injected in an amount of 5 to 15 parts by weight based on 100 parts by weight of amine gas. When the amount of the odor neutralizer injected is less than 5 parts by weight, it cannot sufficiently neutralize remaining amine gas, and when the amount of the odor neutralizer injected is more than 15 parts by weight, it can sufficiently remove the odor of amine gas, but the cost is high. Accordingly, the odor neutralizer may be injected in the amount of 5 to 15 parts by weight based on 100 parts by weight of amine gas An amine gas generator 200 of a second embodiment is the same as the first embodiment in the configuration of the amine supplier 210 and the odor neutralizer supplier 220, but different in that the gassing line 130 and the purging line 140 are integrated into one injection line 230.

An amine gas in the amine gas supplier 210 is supplied to the mold 10 through the injection line 230. A regulator 230 connected to an air tank 250 to maintain the injection pressure of the amine gas at a predetermined level and receiving compressed air heated by the air tank 250 and an air heater 251 is disposed in injection line 230. When compressed air is supplied into the mold 10 through the regulator 231, an amine gas is supplied into the mold 10 or stopped by the amine supplier 210 and the first valve 233 in the injection line 230. The odor neutralizer to be supplied to the injection line 230 is adjusted by a second valve 235 disposed between the odor neutralizer supplier 220 and the injection line 230 and stopping/passing the odor neutralizer.

When a necessary amount of an amine gas is injected into the mold 10, the supply of the amine gas to the injection line 230 through the first valve 233 is stopped and the second valve 235 is opened, so the odor neutralizer is injected with compressed air into the mold 10 and neutralizes the amine gas odor. The first valve 233 and the second valve 235 may be simultaneously controlled by a controller 260. The first valve 233 and the second valve 235 may have a first valve timer 233a and a second valve timer 235a, respectively.

In the related art, when an amine gas supply is stopped, only compressed air is supplied into the mold 10 to discharge the amine gas in the mold to the outside. However, when only compressed air is supplied, as described above, the amine gas remaining in the mold 10 and the amine gas leaking through a gap of the mold gives off a bad smell, so a worker feels discomfort. However, according to the present invention, it is possible to reduce an amine gas odor by supplying an odor neutralizer with compressed air.

A method of neutralizing an amine gas using the amine gas generators 100 and 200 is as follows.

Figure 2:
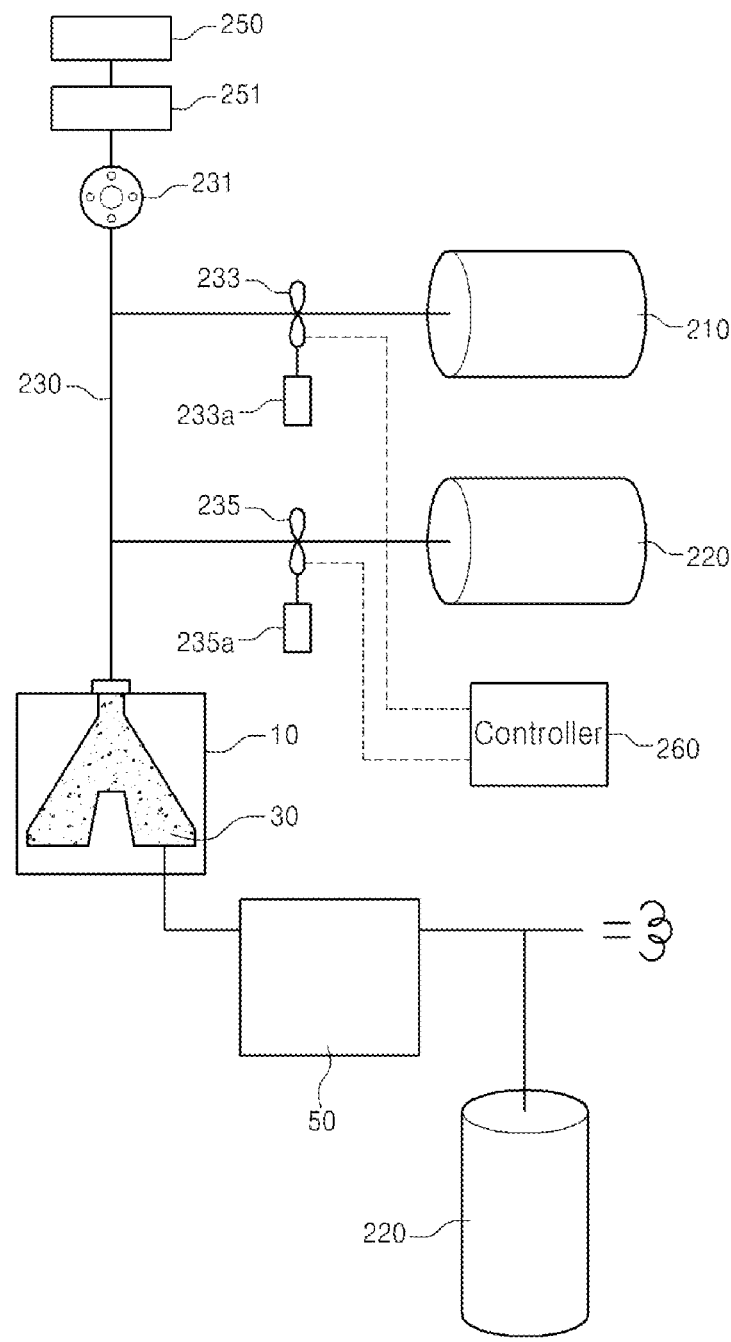
FIG. 2 is a view of an amine gas generator according to a second embodiment of the present invention.
Figure 3:
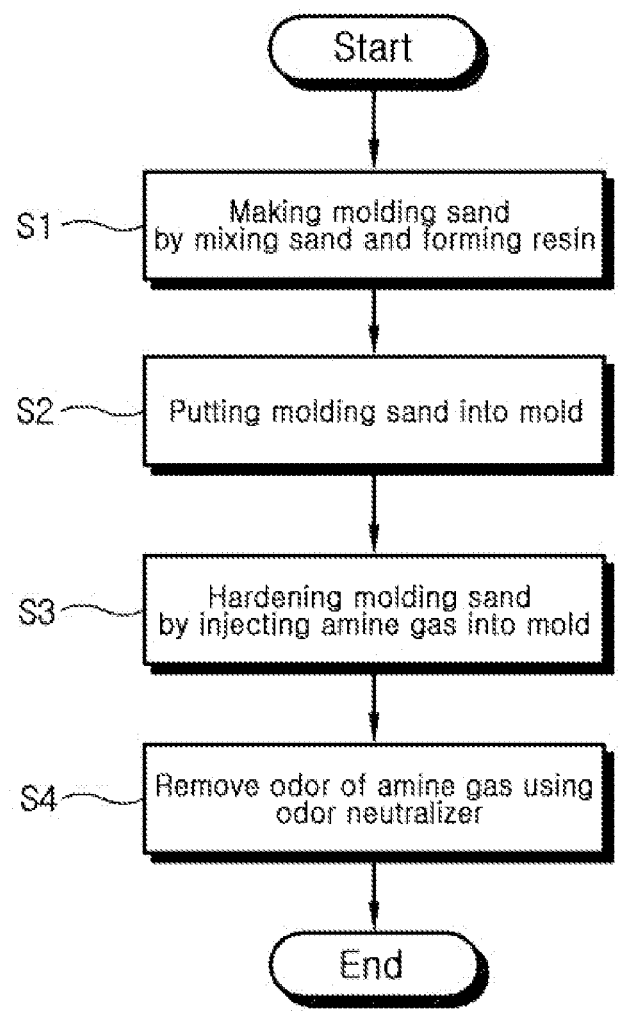
FIG. 3 is a flowchart illustrating a method of neutralizing an amine gas odor according to an embodiment of the present invention.

As shown in FIG. 2, molding sand 30 is made by mixing sand and forming resin (S1).

The sand and the forming resin are used as materials for manufacturing a core or a molding and they are mulled by a blender such as a mixer, thereby making the molding sand 30.

The molding sand 30 is put into the mold 10 (S2).

The molding sand composed of the sand and the forming resin is put into the mold 10 fitting to the shape of a core or a mold. The mold 10 is divided left and right and the molding sand 30 is put into the mold 30 through the upper portion of the mold 10. An amine gas or an odor neutralizer is also injected through the portion for injecting the molding sand 30.

The molding sand 30 is hardened by injecting an amine gas into the mold 10 (S3).

Compressed air and an amine gas are injected into the mold 10 having the shape of a core or a mold and filled with the molding sand 30, through the same inlet of the mold 10. When the amine gas is injected as a catalyst for the molding sand 30 composed of the sand and the forming resin, the forming resin hardens by reacting with the amine gas. When the molding sand is hardened by amine gas, a core or a mold made of polyurethane can be finally obtained.

The amine gas odor is removed by injecting an odor neutralizer (S4).

After the molding sand 30 hardens in the mold 10, the amine gas is discharged into a neutralizing tank 50, and is then neutralized in the neutralizing tank 50 and discharged to the atmosphere. Some of the amine gas may remain in the mold 10 or the amine gas may leak through a gap of the mold 10 while it flows into the neutralizing tank 50, and in this case, the amine gas emits a bad smell discomforting a worker. Accordingly, with discharging of the amine gas, compressed air and an odor neutralizer are injected into the mold 10 through the inlet through which the amine gas was injected. When an odor neutralizer is injected through the inlet of the mold 10, it neutralizes the amine gas remaining in the mold 10 or in the gap of the mold 10, so the distinct odor of ammonia is reduced. Accordingly, a worker does not feel excessively uncomfortable.

Since the odor neutralizer is injected into the mold 10 simultaneously with discharging of the amine gas, there is no additional step and there is no difference between the process time and the process times of the related art, so a worker is not troubled.

In some cases, it may be possible to additionally neutralize the amine gas discharged to the atmosphere through the neutralizing tank 50 by additionally installing the odor neutralizer supplier 120 to the neutralizing tank 50.

The odor neutralizer may be injected in an amount of 5 to 15 parts by weight based on 100 parts by weight of the amine gas. When the amount of the odor neutralizer injected is less than 5 parts by weight, it cannot sufficiently neutralize the remaining amine gas, and when the amount of the odor neutralizer injected is more than 15 parts by weight, the odor neutralizer is too much in comparison to the remaining amine gas, so the odor neutralizer may be wasted.

When the amine gas in the mold 10 or in a gap of the mold 10 remains, a worker may be discomforted by the gas odor. However, as in the present invention, when an odor neutralizer is injected into the mold 10, it neutralizes the amine gas remaining in the mold 10 or in the gap, so a worker can more easily work. Further, since the process of injecting an odor neutralizer is performed simultaneously with discharging of the amine gas from the mold 10, there is no need for an additional process and the work time does not increase, so it is efficient.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An amine gas generator for supplying an amine gas to a mold, comprising:
    an amine supplier for supplying an amine gas;
    a gassing line through which the amine gas of the amine gas supplier is transferred into the mold;
    an odor neutralizer supplier for supplying an odor neutralizer for removing an amine gas odor;
    a purging line through which the odor neutralizer of the odor neutralizer supplier is transferred into the mold;
    an air supplier for supplying a compressed air through the gassing line and the purging line to transfer the amine gas and the odor neutralizer with the compressed air;
    a first regulator for maintaining an injection pressure of the compressed air in the gassing line at a predetermined level;
    a first valve disposed between the amine supplier and the gassing line for selectively stopping or passing the amine gas through the gassing line;
    a second regulator for maintaining an injection pressure of the compressed air in the purging line at a predetermined level;
    a second valve disposed between the odor neutralizer supplier and the purging line for selectively stopping or passing the odor neutralizer through the purging line; and
    a controller for control opening and stopping operation of the first and second valves, said controller configured to open the second valve after, or simultaneously with closing the first valve for supplying the odor neutralizer through the purging line to remove an amine gas odor in the mold.

2. The amine gas generator of claim 1, further comprising:
a first check cylinder disposed in the gassing line for checking a supply amount of the amine gas; and
another valve disposed in the purging line for checking a supply amount of the odor neutralizer.

3. The amine gas generator of claim 1, wherein the first valve has a first valve timer for adjusting opening and closing durations and intervals of the first valve, and
the second valve has a second valve timer for adjusting opening and closing durations and intervals of the second valve.

4. The amine gas generator of claim 1, wherein the air supplier includes:
an air tank for supplying the compressed air; and
an air heater for heating the compressed air discharged from the air tank to a temperature of 40 to 100° C.

5. An amine gas generator for supplying an amine gas to a mold, comprising:
an amine supplier for supplying an amine gas;
an odor neutralizer supplier for supplying an odor neutralizer for removing an amine gas odor;
an injection line through which the amine gas of the amine gas supplier and the odor neutralizer of the odor neutralizer supplier are transferred into the mold;
an air supplier for supplying a compressed air through the injection line to transfer the amine gas and the odor neutralizer with the compressed air;
a regulator for maintaining an injection pressure of the compressed air in the injection line at a predetermined level;
a first valve disposed between the amine supplier and the injection line for selectively stopping or passing the amine gas through the injection line;
a second valve disposed between the odor neutralizer supplier and the injection line for selectively stopping or passing the odor neutralizer through the injection line; and
a controller for control opening and stopping operation of the first and second valves, said controller configured to open the second valve after, or simultaneously with closing the first valve for supplying the odor neutralizer through the injection line to remove an amine gas odor in the mold.

6. The amine gas generator of claim 5, wherein the air supplier includes:
an air tank for supplying the compressed air; and
an air heater for heating the compressed air discharged from the air tank to a temperature of 40 to 100° C.

* * * * *